United States Patent [19]

Luderer et al.

[11] Patent Number: 5,710,007
[45] Date of Patent: Jan. 20, 1998

US005710007A

[54] METHODS FOR DIAGNOSING PROSTATIC ADENOCARCINOMA

[76] Inventors: Albert A. Luderer, 28 Catbrier Rd., Weston, Conn. 06883; Grant D. Carlson, 460 Clark La., Orange, Conn. 06477; Ya-Ting Chen, 111 Park St. #7J, New Haven, Conn. 06511; Thomas F. Soriano, 2 Benz St., Ansonia, Conn. 06401; Robert P. Thiel, 789 Litchfield Turnpike, Bethany, Conn. 06524

[21] Appl. No.: 536,215

[22] Filed: Sep. 29, 1995

[51] Int. Cl.⁶ .................. G01N 33/53; G01N 33/574; G01N 33/542; G01N 33/537

[52] U.S. Cl. .................. 435/7.1; 435/7.23; 435/7.9; 435/7.92; 436/63; 436/64; 436/518

[58] Field of Search ................... 435/7.9, 7.92, 435/7.23, 7.1; 436/63, 64, 518

[56] References Cited

U.S. PATENT DOCUMENTS 5,501,983  3/1996  Lilja et al. .................. 436/518

OTHER PUBLICATIONS

Luderer, A. A. et al, "Measurement of the proportion of free to total prostate–specific antigen improves diagnostic performance of prostate–specific antigen in the diagnostic gray zone of the total prostate–specific antigen" Urology, vol. 42 (2), pp. 187–191, Aug. 1995.

Prestigiacomo A. F. et al, "Clinical usefulness of free and complexed PSA" Scan. J. Clin. Lab. Invest. vol. 55 (Supple. 221), pp. 32–34, Apr. 28, 1995.

Christensson, A. et al, "Serum prostate specific antigen complexed to alpha 1 anti–chymotrypsin as an indicator of prostate cancer" J. Urol. vol. 150 (1) pp. 100–105, Jul. 1993.

Stenman, U.–H. et al, "Serum concentrations of prostate specific antigen and its complex with a1–anti–chymotryspin before diagnosis of prostate cancer" The Lancet, vol. 344, pp. 1594–1598, Dec. 1994.

*Primary Examiner*—Lila Feisee
*Assistant Examiner*—Yvonne Eyler

[57] ABSTRACT

The present invention relates to a method for diagnosing prostatic adenocarcinoma (CAP) in a male human patient without requiring a biopsy. The total prostate specific antigen (PSA) level in the blood or serum of the patient is measured. If the patient has a total PSA level of between 2.5 ng/ml and 20.0 ng/ml, then the free PSA level in the blood or serum of the patient is measured. The proportion of free PSA to total PSA is calculated. If this proportion is less than about 7%, then the patient is diagnosed as having CAP. The present method can also be used on patients that have a total PSA of at least 10.1 ng/ml, but have also had a negative prostate biopsy.

5 Claims, 5 Drawing Sheets

FIGURE 3

| DIAGNOSTIC REPORT | | PATIENT:_____ |
|---|---|---|
| TOTAL PSA | F/T RATIO | DIAGNOSIS |
| 5.0 ng/ml | <7% | CAP |

FIGURE 4

| DIAGNOSTIC REPORT | PATIENT: _____ | |
|---|---|---|
| TOTAL PSA | F/T RATIO | DIAGNOSIS |
| 12.0 ng/ml | < 7% | CAP |

METHODS FOR DIAGNOSING PROSTATIC ADENOCARCINOMA

TECHNICAL FIELD

The present invention relates to a method for diagnosing prostatic adenocarcinoma (CAP) in a male human patient without requiring a biopsy. The total prostate specific antigen (PSA) level in the blood or serum of the patient is measured. If the patient has a total PSA level of between 2.5 ng/ml and 20.0 ng/ml, then the free PSA level in the blood or serum of the patient is measured. The proportion of free PSA to total PSA is calculated. If this proportion is less than about 7%, then the patient is diagnosed as having CAP. The present method can also be used on patients that have a total PSA of at least 10.1 ng/ml, but have also had a negative prostate biopsy.

BACKGROUND ART

Prostate specific antigen (PSA) is recognized as a molecular marker for prostatic adenocarcinoma (CAP). Blood or serum based immunoassays measuring the total PSA level have been commercially available for a number of years. However, the detection of total PSA does not necessarily mean that a patient has CAP. In order to distinguish CAP, a total PSA test has to satisfy two elements: a high sensitivity—the ability to detect disease when present, and a high specificity—the ability to detect true negatives and avoid false positives. From clinical experience, total PSA tests have become accepted as being predictive of CAP if the total PSA level is greater than 10.0 ng/ml. Total PSA values between 0.0 ng/ml and about 3.9 ng/ml have been predictive of no disease being present, with a value of about 2.5 ng/ml being used for men under 60 years old.

PSA is primarily organ-specific, not cancer specific. Thus, PSA in blood or serum can result not only from CAP, but also from normal or hyperplastic prostate tissues. Below 10.0 ng/ml, a total PSA test cannot distinguish benign prostatic disease, such as benign prostatic hyperplasia (or BPH) from CAP. Studies have found that 43% (136/319) of patients with organ-confined CAP have a total PSA value within the normal range of less than 4.0 ng/ml. Moreover, about 25% (148/597) of men with benign prostatic disease have a total PSA value above 4.0 ng/ml. (See Oesterling, J. E., "Prostate Specific Antigen: A Critical Assessment of the Most Useful Tumor Marker for Adenocarcinoma of the Prostate", *J. Urol.*, Vol:145, 907–923, 1991.) Standard medical practice is to biopsy patients having total PSA levels of between 4.0 ng/ml and 10.0 ng/ml because about 30% of those patients have CAP.

One proposed method for detecting CAP is disclosed in Serial Number WO 92/01936 to Hans Lilja et al., (Lilja application), filed Jul. 22, 1991, under the Patent Cooperation Treaty (PCT). In general, the Lilja application discloses using immunoassays to measure free PSA and a complexed form of PSA. Free PSA is a 33 kDa single chain glycoenzyme that is produced by the epithelial cells lining the acini and prostatic ducts of the prostate gland. Complexed PSA refers primarily to a 90 kDa complex of PSA bound to alpha 1-antichymotrypsin (ACT) protein. Free PSA and complexed PSA, and their proportions are applied in the diagnosis of patients with CAP. Throughout, the specification discloses using a combination of a free PSA to total PSA (F/T) proportion and a complexed PSA to total PSA (C/T) proportion for use in diagnosing CAP. No prostate needle biopsies were performed on the patients, and the patients covered a full range of total PSA values. The text provides no guidance as to specifically how one uses these proportions.

SUMMARY OF THE INVENTION

The present invention relates to a method for diagnosing CAP in a male human patient without requiring a biopsy. Presently, if a patient has a total PSA level of 4.0 ng/ml to 10.0 ng/ml, then he must undergo a prostate needle biopsy, an anesthetic-free operation performed transrectally involving substantial pain and discomfort, especially if a sextant biopsy is performed which requires taking six samples. The present method eliminates the need for about 30% of those patients to undergo such a biopsy for initial diagnosis. A patient diagnosed with CAP from the use of the <7% F/T proportion cutoff would need a prostate biopsy to locate the extent and location of CAP in his prostate. Furthermore, presently, if a patient has a total PSA level of 10.1 ng/ml, and a prostate biopsy has been performed which is negative, the physician is in a quandary as to whether he should continue taking biopsies from the patient now or send the patient home and wait six months. Values of less than 7% for the F/T PSA proportion indicate the presence of CAP and the immediate need to confirm the extent and location of disease with a biopsy.

As used for patients, in general, the present method comprises four steps. First, one measures the PSA level in the blood or serum of the patient. Second, one measures the free PSA level in the blood or serum of a patient, but only if he has a total PSA level of between 2.5 ng/ml and 20.0 ng/ml. (As in the past, if the patient has a total PSA level below 2.5 ng/ml, then he is diagnosed to have benign prostatic disease. If the patient has a total PSA level above 20.0 ng/ml, then he is diagnosed as having CAP.) Third, one calculates the proportion of free PSA to total PSA. Fourth and finally, one diagnoses the patient as having CAP if the calculated proportion of free PSA to total PSA is less than about 7%.

Another embodiment of the present invention is a report for a diagnosis of a male human patient having CAP without requiring a biopsy. This report comprises listing a total PSA level of between 2.5 ng/ml and 20.0 ng/ml and listing a free PSA to total PSA proportion which is less than about 7%.

As used for patients who have a total PSA level of at least 10.1 ng/ml and have already been biopsied, but with negative results, the present method also comprises three steps. First, one measures the free PSA level in the blood or serum of the patient. (Optionally, one can re-measure the total PSA level in the blood or serum of the patient.) Then, one calculates the proportion of free PSA to total PSA. Finally, one diagnoses the patient as having CAP if the calculated proportion of free PSA to total PSA is less than about 7%, without requiring a further prostate biopsy to confirm CAP.

A further embodiment of the present invention is a report for a diagnosis of a male human patient having CAP who has a total PSA level of at least 10.1 ng/ml and has had a negative prostate biopsy without requiring a further prostate biopsy to confirm CAP. This report comprises a listing a total PSA level of between 10.1 ng/ml and 20.0 ng/ml and a listing of a free PSA to total PSA proportion which is less than about 7%.

BRIEF DESCRIPTION OF THE DRAWINGS

FIG. 3 is a view of a pathology report according to the present invention.

FIG. 4 is a view of a pathology report according to the present invention wherein the patient has already been determined to have a total PSA level of at least 10.1, but has had a negative biopsy.

PREFERRED EMBODIMENTS

Assays

Figure 1:
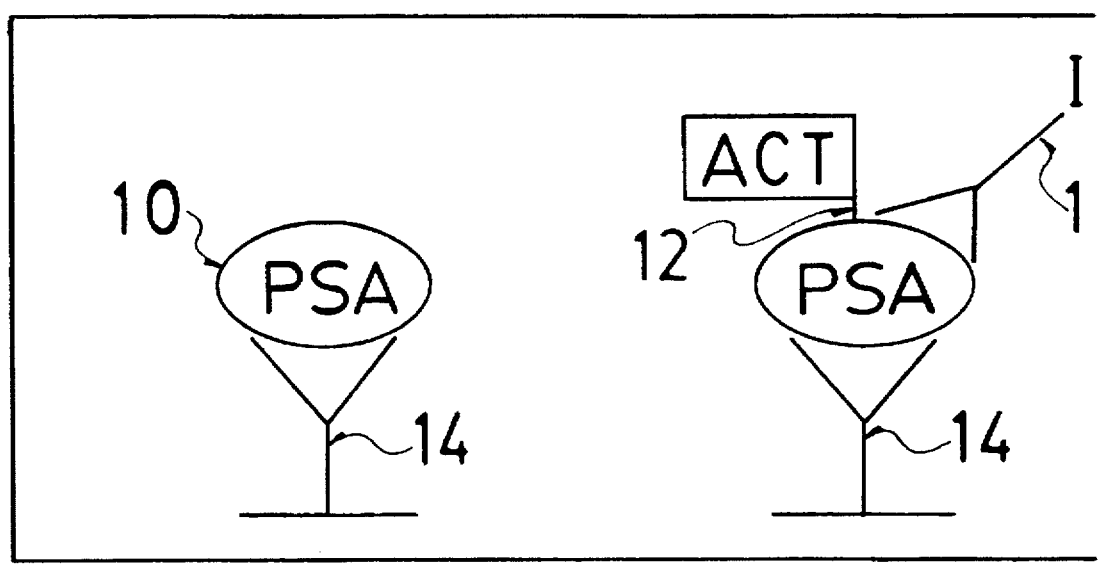
FIG. 1 is a diagrammatic view of the total PSA assay used in the present invention.

In a preferred embodiment, the present method comprises two immunoassays. The first assay is a total PSA sandwich immunoassay manufactured by Tosoh Medics, Inc. (Tosoh) of Foster City, Calif. The assay is an immunoenzymetric assay using dual murine monoclonal antibodies. FIG. 1 shows diagrammatically how, in the final sandwich configurations, this first assay captures both free PSA (10) and complexed PSA/ACT (12) using a capture antibody (14) and an enzyme labelled antibody (16).

Figure 2:
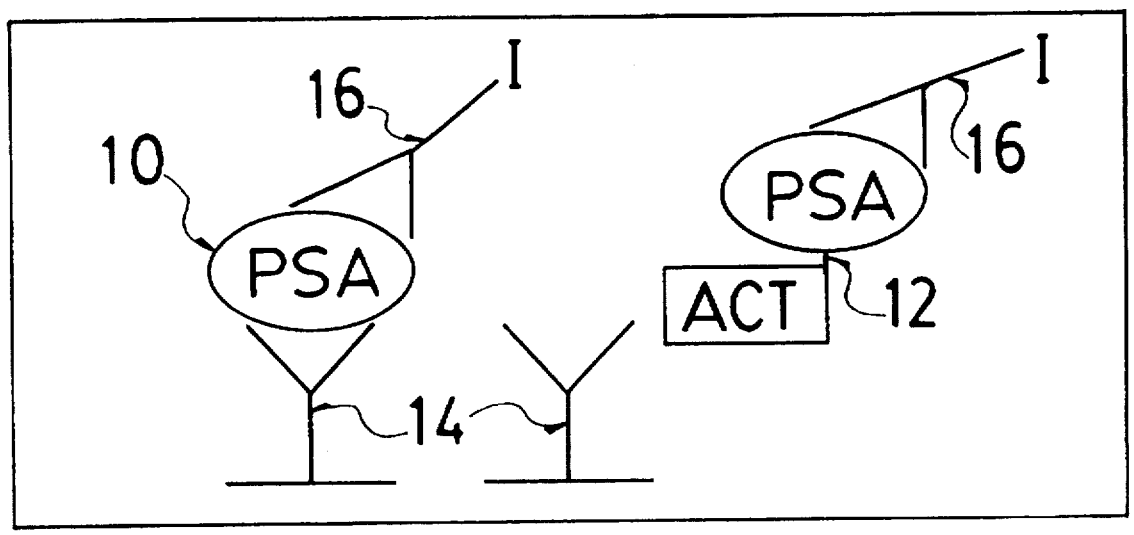
FIG. 2 is a diagrammatic view of the free PSA assay used in the present invention.

The second assay is a free PSA immunoassay manufactured developed by Immuno Corp. for Dianon Systems, Inc. (Dianon) of Stratford, Conn. This free PSA test is designed to detect free PSA in serum using an IRMA coated tube format. Free PSA binds to a tube coated by a monoclonal antibody which selectively binds free PSA but not complexed PSA. After washing, an $I^{125}$ labelled polyclonal antibody against free PSA is reacted with the bound free PSA. The physician is given a result that expresses a proportion of free PSA to total PSA. FIG. 2 shows diagrammatically how in the final sandwich configuration, this second assay captures free PSA (10), but the capture antibody (14) does not specifically bind to the complex of the PSA/ACT complex (12) and radio-labelled antibody (16).

EXAMPLE

In a clinical study to validate the present invention, 334 patients were tested. Classified as "BENIGN", 90 males were identified as being between 45 years old and 75 years old, having benign prostate disease histologically confirmed by sextant needle prostate biopsy, and no history of cancer. The age mean was 65. Classified as "CAP", 174 males were identified as being between 45 years old and 75 years old and having primary CAP histologically confirmed by needle prostate biopsy. The age mean was 67. None of the above patients received any form of prostate-related treatment prior to blood draw. Total PSA was measured using the Tosoh assay described above, in accordance with the manufacturer's instructions. Free PSA was measured using the Dianon assay described above, in accordance with the manufacturer's instructions.

The patient sample was split on the basis of age between those over 60 years old and those 60 years and under. It was further split between those having a total PSA level of between 2.5 ng/ml and 10.0 ng/ml and those having a total PSA level of between 10.1 and 20.0 ng/ml. These splits were determined on the basis of a logistic regression to assess the relative contribution of free PSA, total PSA, and age to the probability that a patient will be confirmed as having CAP on sextant, six core biopsy performed.

Table 1 outlines the results of total PSA testing for patients in the 2.5 to 10.0 ng/ml range.

TABLE 1

| STATUS | CAP | BENIGN | CAP | BENIGN | CAP | BENIGN |
|---|---|---|---|---|---|---|
| Patient Age | 60 and under | | >60 | | All ages | |
| No. Patients (Total PSA level) | 12 | 47 | 78 | 127 | 90 | 174 |
| Mean | 6.2 | 5.7 | 6.4 | 5.9 | 6.3 | 5.8 |
| Median | 6.5 | 5.5 | 6.3 | 5.6 | 6.3 | 5.6 |
| Std. Dev.* | 2.3 | 1.8 | 1.8 | 1.9 | 1.9 | 1.9 |
| 95% CL** | (4.7–7.8) | (5.1–6.2) | (5.9–6.8) | (5.6–6.3) | (5.9–6.7) | (5.6–6.1) |
| p-values*** | 0.45 | | 0.10 | | 0.05 | |

*standard deviation
**95% confidence level for the mean
***p-values for medians using the Wilcoxon test comparing median values between BENIGN and CAP patients As can be seen from this data, total PSA testing does not discriminate between CAP and benign prostate disease patients in the 2.5 to 10.0 ng/ml range. The failure to discriminate is consistent regardless of patient age.

Table 2 outlines the results of free PSA to total PSA testing for the patients in Table 1.

TABLE 2

| STATUS | CAP | BENIGN | CAP | BENIGN | CAP | BENIGN |
|---|---|---|---|---|---|---|
| Patient Age | 60 and under | | >60 | | All ages | |
| No. Patients | 12 | 47 | 78 | 127 | 90 | 174 |

TABLE 2-continued

| STATUS | CAP | BENIGN | CAP | BENIGN | CAP | BENIGN |
|---|---|---|---|---|---|---|
| (F/T PSA %) | | | | | | |
| Mean | 11 | 17 | 16 | 22 | 14 | 21 |
| Median | 11 | 17 | 14 | 20 | 13 | 19 |
| Std. Dev.* | 5 | 8 | 8 | 10 | 8 | 10 |
| 95% CL** | (8–15) | (15–20) | (13–17) | (20–24) | (13–16) | (19–22) |
| p-values*** | 0.007 | | <0.0001 | | <0.001 | |

*standard deviation
**95% confidence level for the mean
***p-values for medians using the Wilcoxon test comparing median values between BENIGN and CAP patients One can clearly see that the use of free to total PSA testing produces a separation of the median values of patients having CAP from those having benign prostate disease. This separation is significant across all ages.

For patients having a total PSA level of between 10.1 ng/ml and 20.0 ng/ml, Table 3 shows that the addition of calculating the F/T PSA proportion does not indicate how to differentiate between all patients having CAP and those having benign prostate disease. However, Table 3 does show that the addition of calculating the F/T PSA proportion indicates that one can differentiate between patients having CAP and those having benign prostate disease if the patients are over 60, rathern than 60 and under.

TABLE 3

| STATUS | CAP | BENIGN | CAP | BENIGN | CAP | BENIGN |
|---|---|---|---|---|---|---|
| Patient Age | 60 and under | | >60 | | All ages | |
| No. Patients | 4 | 5 | 38 | 23 | 42 | 28 |
| (Total PSA level) | | | | | | |
| Mean | 13.6 | 12.1 | 14.1 | 13.5 | 14.1 | 13.3 |
| Median | 12.7 | 12.2 | 14.0 | 12.4 | 14.0 | 12.3 |
| Std. Dev.* | 3.8 | 1.3 | 2.3 | 2.9 | 2.5 | 2.7 |
| 95% CL** | (7.4 to 19.7) | (10.5 to 13.8) | (13.4 to 14.9) | (12.3 to 14.9) | (13.3 to 14.9) | (12.2 to 14.3) |
| p-values*** | 0.62 | | 0.33 | | 0.15 | |
| (F/T PSA %) | | | | | | |
| Mean | 13 | 14 | 13 | 20 | 13 | 19 |
| Median | 10 | 15 | 12 | 20 | 12 | 17 |
| Std. Dev.* | 9 | 5 | 5 | 10 | 5 | 9 |
| 95% CL** | (0–27) | (9–20) | (13–17) | (16–25) | (11–15) | (16–23) |
| p-values*** | 0.46 | | 0.001 | | 0.002 | |

*standard deviation
**95% confidence level for the mean
***p-values for medians using the Wilcoxon test comparing median values between BENIGN and CAP patients However, it has been discovered that a log-linear logit model of the above data in Tables 1 to 3 does reveal that the use of a <7% cutoff level for the F/T PSA proportion enables the physician to differentiate between CAP patients and benign prostate disease patients. Table 4 demonstrates the findings of this modeling.

TABLE 4

| | Percent probability that the patient has CAP | | | | | |
|---|---|---|---|---|---|---|
| Patient Age | 60 and under | | >60 | | All ages | |
| Total PSA** | <10.0 | >10.0 | <10.0 | >10.0 | <10.0 | >10.0 |
| (F/T PSA) | | | | | | |
| <7% | 84 | 92 | 95 | 98 | 92 | 97 |

TABLE 4-continued

| | Percent probability that the patient has CAP | | | | | |
|---|---|---|---|---|---|---|
| ≧7%–15% | 26 | 45 | 56 | 75 | 48 | 71 |
| 16%–25% | 10 | 20 | 28 | 48 | 25 | 46 |
| >25% | 3 | 7 | 10 | 21 | 9 | 20 |

*based on logit linear model
**"<10.0" refers to a total PSA range of between 2.5 and 10.0 ng/ml, while ">10.0" refers to a total PSA range of between 10.1 and 20.0 ng/ml.

Figure 5:
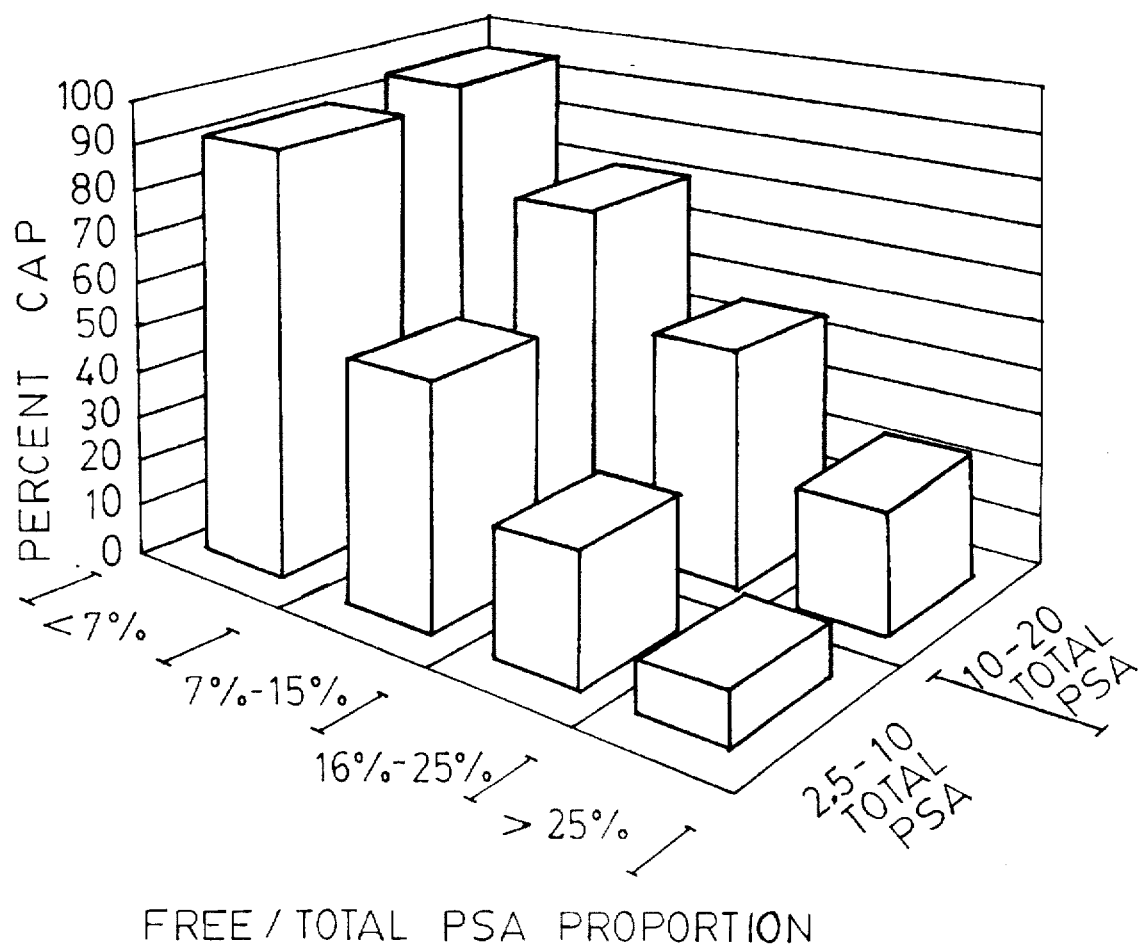
FIG. 5 is a graph showing the distribution of F/T proportions versus the probability of a patient having CAP.

Overall, the model predicts a 95% probability for a patient having CAP that can be confirmed by sextant prostate biopsy using the <7% F/T proportion cutoff. For patients in the total PSA range of 2.5 to 10.0 ng/ml, the use of a F/T proportion cutoff of <7% gives an overall 92% chance of the patient having CAP. As recognized by physicians, a probability of greater than 80% in these cases is regarded as sufficient to diagnose CAP, absent any contraindications. FIG. 5 shows the distribution of the F/T proportion in the sample patients. Clearly the CAP patients can be separated benign prostate disease patients by using the about <7% F/T proportion cutoff mark.

Using the present method, and in view of the above clinical data, one can expect the following scenario for every 100 prostate biopsies performed on males having a F/T proportion of less than about 7%—about 90 will have a diagnosis of CAP confirmed by the biopsy. In a time of increasing concern about health care costs and unnecessary medical procedures, the present method provides a powerful cost-saving clinical tool to the urologist. Using the present method, physicians can confidently order a prostate biopsy for a first-time patient having a total PSA level of between 2.5 ng/ml and 10.0 ng/ml, or reorder a prostate biopsy for those patients having a total PSA level of between at least 10.1 ng/ml to 20 ng/ml, but have had a prior negative biopsy.

FIG. 3 and 4 illustrates pathology reports that use the present method. In FIG. 3, the report includes a listing of the results of a first assay for total PSA. The total PSA level for the patient is between 2.5 ng/ml and 10 ng/ml. It also includes a listing of a calculation occurring from a free PSA assay—the free PSA to total PSA proportion. The F/T proportion is less than about 7%. Finally, the report includes a diagnosis of the patient as having CAP. FIG. 4 is a report for a patient that is being re-measured. The report includes a listing of the results of a first assay for total PSA, showing a total PSA level of at least about 10.1 ng/ml. It also includes a listing of a calculation occurring from a free PSA assay—the free PSA to total PSA proportion. The F/T proportion is less than about 7%. Finally, the report includes a diagnosis of the patient as having CAP.

All publications or unpublished patent applications mentioned herein are hereby incorporated by reference thereto.

Other embodiments of the present invention are not presented here which are obvious to those of skill in the art, now or during the term of any patent issuing herefrom, and thus, are within the spirit and scope of the present invention.

We claim:

1. A method for diagnosing prostatic adenocarcinoma (CAP) in a male human patient without requiring a prostate biopsy comprising:

a) measuring the total prostate specific antigen (PSA) level in the blood or serum of the patient;

b) measuring the free PSA level in the blood or serum of a patient only if he has a total PSA level of between 2.5 ng/ml and 20.0 ng/ml;

c) calculating the proportion of free PSA to total PSA; and d) diagnosing the patient as having CAP if the calculated proportion of free PSA to total PSA is less than about 7%.

2. A method for diagnosing prostatic adenocarcinoma (CAP) in a male human patient who has a measured total prostate specific antigen (PSA) level of at least 10.1 ng/ml and has had a negative prostate biopsy without requiring a further prostate biopsy to confirm CAP comprising:

a) measuring the free PSA level in the blood or serum of the patient;

b) calculating the proportion of free PSA to total PSA; and c) diagnosing the patient as having CAP if the calculated proportion of free PSA to total PSA is less than about 7%.

3. The method for diagnosing prostatic adenocarcinoma (CAP) as in claim 2 wherein one also re-measures the total prostate specific antigen (PSA) level in the blood or serum of the patient.

4. The method for diagnosing prostatic adenocarcinoma (CAP) as set forth in claim 2 wherein the total prostate specific antigen (PSA) level in the blood or serum of the patient is between 10.1 ng/ml and 20.0 ng/ml.

5. The method for diagnosing prostatic adenocarcinoma (CAP) as set forth in claim 3 wherein the total prostate specific antigen (PSA) level in the blood or serum of the patient is between 10.1 ng/ml and 20.0 ng/ml.

* * * * *